(12) United States Patent
Carlsson et al.

(10) Patent No.: US 11,253,543 B2
(45) Date of Patent: Feb. 22, 2022

(54) DIALYSIS PRECURSOR COMPOSITION PRODUCT

(71) Applicant: GAMBRO LUNDIA AB, Lund (SE)

(72) Inventors: Ola Carlsson, Lund (SE); Lennart Jonsson, Bjarred (SE); Torbjorn Linden, Hasslo (SE); Anders Wieslander, Lund (SE)

(73) Assignee: GAMBRO LUNDIA AB, Lund (SE)

( * ) Notice: Subject to any disclaimer, the term of this patent is extended or adjusted under 35 U.S.C. 154(b) by 117 days.

(21) Appl. No.: 15/800,719

(22) Filed: Nov. 1, 2017

(65) Prior Publication Data
US 2018/0050062 A1 Feb. 22, 2018

Related U.S. Application Data

(62) Division of application No. 13/805,474, filed as application No. PCT/EP2011/060233 on Jun. 20, 2011, now abandoned.

(60) Provisional application No. 61/358,006, filed on Jun. 24, 2010.

(51) Int. Cl.
| | |
|---|---|
| *A61K 33/14* | (2006.01) |
| *A61K 9/00* | (2006.01) |
| *A61K 31/185* | (2006.01) |
| *A61K 31/7004* | (2006.01) |
| *A61K 33/00* | (2006.01) |
| *A61K 33/06* | (2006.01) |
| *A61K 33/10* | (2006.01) |
| *A61K 31/19* | (2006.01) |
| *A61K 31/191* | (2006.01) |
| *A61K 31/194* | (2006.01) |
| *A61M 1/16* | (2006.01) |
| *A61M 1/28* | (2006.01) |

(52) U.S. Cl.
CPC ............ *A61K 33/14* (2013.01); *A61K 9/0029* (2013.01); *A61K 9/0095* (2013.01); *A61K 31/185* (2013.01); *A61K 31/19* (2013.01); *A61K 31/191* (2013.01); *A61K 31/194* (2013.01); *A61K 31/7004* (2013.01); *A61K 33/00* (2013.01); *A61K 33/06* (2013.01); *A61K 33/10* (2013.01); *A61M 1/1666* (2014.02); *A61M 1/287* (2013.01)

(58) Field of Classification Search
CPC .... A61K 2300/00; A61K 33/00; A61K 33/06; A61M 1/287
See application file for complete search history.

(56) References Cited

U.S. PATENT DOCUMENTS

| | | | | |
|---|---|---|---|---|
| 3,560,380 | A * | 2/1971 | Stade ............... | A61M 1/1654 252/1 |
| 4,581,141 | A * | 4/1986 | Ash .................. | A61M 1/1696 210/321.84 |
| 4,636,412 | A | 1/1987 | Field | |
| 4,756,838 | A * | 7/1988 | Veltman ............. | A61M 1/1654 210/646 |
| 6,610,206 | B1 | 8/2003 | Callan et al. | |
| 9,029,333 | B2 | 5/2015 | Sugiyama et al. | |
| 2004/0019313 | A1 | 1/2004 | Childers et al. | |
| 2004/0057885 | A1 | 3/2004 | Taylor | |
| 2004/0060865 | A1 * | 4/2004 | Callan ................ | A61K 31/19 210/646 |
| 2007/0087212 | A1 | 4/2007 | Iyengar et al. | |
| 2007/0231395 | A1 | 10/2007 | Kai et al. | |
| 2008/0015487 | A1 | 1/2008 | Szamosfalvi et al. | |
| 2009/0306002 | A1 | 12/2009 | Nakanishi et al. | |
| 2010/0120702 | A1 * | 5/2010 | Sugiyama ............ | A61K 31/194 514/23 |
| 2011/0172583 | A1 | 7/2011 | Callan et al. | |
| 2012/0291875 | A1 | 11/2012 | Shah et al. | |

FOREIGN PATENT DOCUMENTS

| | | |
|---|---|---|
| CN | 1938058 | 3/2007 |
| EP | 0034916 | 9/1981 |
| EP | 0399918 | 11/1990 |
| EP | 0417478 | 3/1991 |
| EP | 0602014 | 6/1994 |
| EP | 0602921 | 6/1994 |
| EP | 1059083 | 12/2000 |
| EP | 1101483 | 5/2001 |
| EP | 1192961 | 4/2002 |
| EP | 1714657 | 10/2006 |
| EP | 1731183 | 12/2006 |

(Continued)

OTHER PUBLICATIONS

Ahmad et al., "Dialysate Made From Dry Chemicals Using Citric Acid Increases Dialysis Dose," American Journal of Kidney Diseases, vol. 35, No. 3 Mar. 2000: pp. 493-499.
Gabutti et al., "Citrate- vs. acetate-based dialysate in bicarbonate haemodialysis: consequences on haemodynamics, coagulation, acid-base status, and electrolytes," BMC Nephrology 2009, 10:7.
Nilsson, "Citrate vs. Acetate In Bicarbonate-Based Dialysis Fluid—What Does it Mean Clinically?" Gambro Lundia AB, 2012.
Japanese Office Action for Japanese Application No. 2013-515839, dated Apr. 21, 2015.
Japanese Office Action for Japanese Application No. 2013-515839, dated Jul. 28, 2015.
Gambro Lundia AB's Response to Opposition filed in related European patent application No. 11729087.4 on Aug. 5, 2016.

(Continued)

*Primary Examiner* — Michael B. Pallay
(74) *Attorney, Agent, or Firm* — K&L Gates LLP

(57) ABSTRACT

The present invention concerns a dialysis acid precursor composition for use during preparation of a dialysis acid concentrate solution and for mixing with water, a sodium containing concentrate, and a bicarbonate containing concentrate into a ready-for-use dialysis solution. The dialysis acid precursor composition consists of powder components comprising glucose, at least one dry acid and at least one magnesium salt, and optionally potassium salt, and calcium salt. According to the invention the glucose and the at least one magnesium salt, are present as anhydrous components in the dialysis acid precursor composition.

12 Claims, No Drawings

(56) References Cited

FOREIGN PATENT DOCUMENTS

| EP | 1834652 | 9/2007 |
|---|---|---|
| EP | 2119438 | 11/2009 |
| EP | 2123270 | 11/2009 |
| EP | 2151247 | 2/2010 |
| EP | 2286820 | 2/2011 |
| FR | 2766797 | 2/1999 |
| JP | 04-257522 | 9/1992 |
| JP | H1087478 | 4/1998 |
| JP | 2003104869 | 4/2003 |
| JP | 2005-206572 | 8/2005 |
| RU | 2311202 C1 | 11/2007 |
| TW | 200911287 | 3/2009 |
| WO | 92/11046 | 7/1992 |
| WO | 0057935 | 10/2000 |
| WO | 01/21233 | 3/2001 |
| WO | 03/043680 | 5/2003 |
| WO | 2005002599 | 1/2005 |
| WO | 2010/055963 | 5/2010 |
| WO | 2010/112570 | 10/2010 |
| WO | 2010112570 | 10/2010 |
| WO | 2011/161055 | 12/2011 |
| WO | 2011/161056 | 12/2011 |
| WO | 2012/175353 | 12/2012 |
| WO | 2012/175354 | 12/2012 |
| WO | 2013/004362 | 1/2013 |

OTHER PUBLICATIONS

Kipouros et al., "A Thermal Analysis of the Production of Anhydrous MgCl2," Journal of Light Metals, May 2001 (reference D4 cited in Response to Opposition filed in related European patent application No. 11729087.4 on Aug. 5, 2016).
Declaration of David Karlsson relating to film thickness, dated Jul. 29, 2016 (reference D5 cited in Response to Opposition filed in related European patent application No. 11729087.4 on Aug. 5, 2016).
Annex A (curriculum vitae) of David Karlsson Declaration (annex to reference D5 cited in Response to Opposition filed n related European patent application No. 11729087.4 on Aug. 5, 2016).
Translation Declaration signed by Don Sanderson on Jul. 22, 2016 attesting to the translation of selected paragraphs of JP 10-87478 (reference D2 cited by opponent Fresenius Medical Care), (reference D6 cited in Response to Opposition filed in related European patent application No. 11729087.4 on Aug. 5, 2016).
Experimental annex providing stability data (reference D7 cited in Response to Opposition filed in related European patent application No. 11729087.4 on Aug. 5, 2016).
Ing T.S. et al., Employing L-lactic acid powder in the preparation of a dry "acid concentrate" for use in a bicarbonate-based dialysis solution-generating system: experience in hemodialysis patients, The International Journal of Artificial Organs, 1994, vol. 17, nr 2, p. 70-73.
Gärtner, Heinz, "Developments in barrier films," Symposium "Sperrschichtfolien [Barrier films]" on Jun. 30/Jul. 1, 2004, Würzburg, Germany.
TW200911287 Application—Incomplete Translation—p. 1 is missing.
TW200911287—Translation of Office Action—8 pages.
Barry et al. (Basis for Using Moisture Vapor Transmission Rate Per Unit Product in The Evaluation of Moisture-Barrier Equivalence of Primary Packages for Solid Oral Dosage Forms, 2004).
CurTec article (http://www.pharmaceutical-networking.com/moisture-resistant-packaging/) 2015.
Nikhil Mehrotra (Masters Theses): A Study of Water Vapor Transmission Rate of Blister Packs By USP Standard and Continuous Gravimetric Protocol 2010.
International Search Report cited in PCT/EP2012/060969 dated Oct. 2, 2012.
Sigma-Aldrich Product Spedification form for Calcium Chloride; downloaded Mar. 15, 2016.
Norner AS download showing WVTR calculation for: FEP layer (1-mm); downloaded Feb. 13, 2015.
Norner AS download showing WVTR calculation for: PMMA layer (1-mm); downloaded Feb. 14, 2015.
Norner AS download showing WVTR calculation for: PTFE layer (1-mm); downloaded Feb. 14, 2015.
Norner AS download showing WVTR calculation for: PTFE-PTFE dual-layer (1-mm); downloaded Feb. 14, 2015.
Norner AS download showing WVTR calculation for: PTFE layer (2-mm); downloaded Feb. 14, 2015.
Norner AS download showing WVTR calculation for: PVDC layer (1-mm); downloaded Feb. 13, 2015.
Norner AS download showing WVTR calculation for: PTFE-PMMA dual-layer (1-mm); downloaded Feb. 14, 2015.
Oracle Packaging; data for aluminum foil; downloaded Feb. 16, 2015.
International Search Report cited in PCT/EP2012/060971 dated Aug. 21, 2012.
Magnesium chloride 4.5 hydrate, European Pharmacopoeia 7.3 Jan. 2012.
International Preliminary Report on Patentability for International Application No. PCT/EP2012/075008, dated Jun. 24, 2014.
International Search Report for International Application No. PCT/EP2012/075008, dated Mar. 6, 2013.
Written Opinion of the International Searching Authority for International Application No. PCT/EP2012/075008, dated Mar. 6, 2013.
International Preliminary Report on Patentability for International Application No. PCT/EP2012/075007, dated Jun. 24, 2014.
International Search Report for International Application No. PCT/EP2012/075007, dated Mar. 6, 2013.
Written Opinion of the International Searching Authority for International Application No. PCT/EP2012/075007, dated Mar. 6, 2013.
Search Report for related International Patent Application No. PCT/EP2013/054386 dated May 23, 2013 (6 pages).
Written Opinion for related International Patent Application No. PCT/EP2013/054386 dated May 23, 2013 (5 pages).
English translation of Japanese Office Action dated Nov. 22, 2016 in corresponding Japanese application No. 2014-560335 (4 pages).
Vortrag Dr. Gartner mit dem Titel, "Entwicklungen bei Sperrschichtfolien", ("Fachtagung, Sperrschichtfolien" vom 30. Jun./Jul. 1, 2004 in Wurzburg) nebst eidesstattlicher Versicherung des Hernn Dietmar Hansel (reference D3 cited in Notice of Opposition filed in related European patent application No. case No. 11729087.4-1453 / 2585076 by Fresenius Medical Care AG & Co. KGaA on Dec. 3, 2015) (35 pages).
Summons to attend oral proceedings pursuant to Rule 115(1) EPC issued in related European Patent case No. 11729087.4-1453 / 2585076 on Aug. 30, 2016 (9 pages).
Observations (Experimental Data) filed in related European patent application No. case No. 11729087.4-1453 / 2585076 by Gambro Lundia AB on Aug. 5, 2016 (5 pages).
Declaration of Ola Carlsson filed in related European patent application No. case No. 11729087.4-1453 / 2585076 by Gambro Lundia AB on Aug. 5, 2016 (13 pages).
Notice of Opposition filed in related European Patent case No. 11729087.4-1453 / 2585076 by Fresenius Medical Care AG & Co. KGaA on Dec. 3, 2015 (16 pages).

* cited by examiner

DIALYSIS PRECURSOR COMPOSITION PRODUCT

PRIORITY CLAIM

This application is a divisional application of U.S. patent application Ser. No. 13/805,474, entitled, "DIALYSIS PRECURSOR COMPOSITION", filed on Mar. 14, 2013, which is a U.S. National Phase of International Application No. PCT/EP2011/060233, filed on Jun. 20, 2011, which claims priority to U.S. Provisional Application No. 61/358,006, filed on Jun. 24, 2010, and Swedish Patent Application No. 1050685-5, filed on Jun. 23, 2010, the entire contents of each of which are incorporated herein by reference.

TECHNICAL FIELD

The present invention concerns a dialysis acid precursor composition for use during preparation of a dialysis acid concentrate solution and for further mixing with water, a sodium containing concentrate, and a bicarbonate containing concentrate into a ready-for-use dialysis solution. The present invention further concerns a method of providing a dialysis acid concentrate solution for dilution with water, a sodium containing concentrate, and a bicarbonate containing concentrate to produce a ready-for-use dialysis solution

BACKGROUND

When a person's kidney does not function properly uremia is developed. Dialysis is a well established treatment technique for uremia. Essentially, dialysis artificially replaces the functions of the kidney. There are two distinct types of dialysis, hemodialysis and peritoneal dialysis.

Hemodialysis involves withdrawing blood from the body and cleaning it in an extracorporeal blood circuit and then returning the cleansed blood to the body. The extracorporeal blood circuit includes a dialyzer which comprises a semipermeable membrane. The semipermeable membrane has a blood side and a dialysate side, and waste substances and excess fluid is removed from the blood passing on the blood side of the semipermeable membrane through the semipermeable membrane over to the dialysate side of the semipermeable membrane.

Hemodialysis may be performed in three different treatment modes, hemodialysis, hemofiltration, and hemodiafiltration. Common to all three treatment modes is that the patient is connected by a blood line to the dialysis machine, which continuously withdraws blood from the patient. The blood is then brought in contact with the blood side of the semipermeable membrane within the dialyzer in a flowing manner.

In hemodialysis, an aqueous solution called dialysis solution is brought in contact with the opposite membrane surface, the dialysate side, in a flowing manner. Waste substances (toxins) and solutes are removed/controlled mainly by diffusion. Excess fluid is removed by applying transmembrane pressure over the semipermeable membrane. Solutes and nutrients may diffuse in the opposite direction from the dialysis solution, through the semipermeable membrane and into the blood.

In hemofiltration, no dialysis solution is brought in contact with the dialysate side of the semipermeable membrane. Instead only a transmembrane pressure is applied over the semipermeable membrane thereby removing fluid and waste substances from the blood through the semipermable membrane wall and into the dialysate side thereof (convective flow). Fluid and waste substances are then passed to drain. To replace some of the removed fluid, a correctly balanced electrolyte/buffer dialysis solution (also named infusion fluid or replacement fluid) is infused into the extracorporeal blood circuit. This infusion may be done either pre the dialyzer (pre-infusion mode) or post the dialyzer (post-infusion mode) or both.

Hemodiafiltration is a combination of hemodialysis and hemofiltration, a treatment mode that combines transport of waste substances and excess fluids through the semipermeable wall by both diffusion and convection. Thus, here a dialysis solution is brought in contact with the dialysate side of the semipermeable membrane in a continuously flowing manner, and a dialysis solution (also named infusion fluid or replacement fluid) is used for infusion into the extracorporeal blood circuit in pre-infusion mode, post-infusion mode or both.

For many patients, hemodialysis is performed for 3-5 hours, three times per week. It is usually performed at a dialysis centre, although home dialysis is also possible. When home dialysis is performed patients are free to perform dialysis more frequently and also in more gentle treatments with longer treatment times, i.e. 4-8 hours per treatment and 5-7 treatments per week. The dose and treatment times may be adjusted due to different demand of the patients.

In the case of patients suffering from acute renal insufficiency, a continuous treatment, throughout a major portion of the entire day for up to several weeks, a continuous renal replacement therapy (CRRT), or intermittent renal replacement therapy (IRRT) is the indicated treatment depending on the patients status. Also here the removal of waste substances and excess fluid from the patient is effected by any or a combination of the treatment modes hemodialysis, hemofiltration and hemodiafiltration.

In a peritoneal dialysis treatment a hypertonic dialysis solution is infused into the peritoneal cavity of the patient. In this treatment solutes and water is exchanged in the capillary vessels of a patient's peritoneal membrane with the hypertonic dialysis solution. The principle of this method is diffusion of solutes transferred according to the concentration gradient and water migration due to the osmotic differences over the peritoneal membrane.

The dialysis solutions used in all the above dialysis techniques contain mainly electrolytes like sodium, magnesium, calcium, potassium, an acid/base buffer system and optionally glucose or a glucose-like compound. All the components in dialysis solutions are selected to control the levels of electrolytes and the acid-base equilibrium within the blood and to remove waste materials from the blood.

Dialysis solutions are today prepared from different types of concentrates. It may be liquid concentrates of different degree of concentration, where the acid/electrolyte part is separated from the buffer part. It may be provided in highly concentrated volumes of 1-8 L in bags for bedside use, or in more diluted concentrated volumes of 5-20 L in canisters, which still are for bedside use. Concentrates may also be prepared in central tanks in volumes of 300-1000 L.

When using bicarbonate as a buffer component in the dialysis solution, bicarbonate is often provided as a dry concentrate for on-line-preparation of saturated bicarbonate containing concentrate. The saturated bicarbonate containing concentrate is thereafter mixed with an acid/electrolyte concentrate and further diluted with purified water to produce the on-line prepared dialysis solution.

Dialysis solutions have improved in quality over the years, and the availability of concentrated precursor compositions for further dilution and mixing with other components into a ready-for-use dialysis solution have decreased the costs and improved the environmental issues.

One way to further limit the costs and improve the environmental issues would be to provide a dialysis precursor composition in which all component are dry. However, having all components as dry components adds new problems.

Firstly, dry acid and bicarbonate powder are not compatible. When small amounts of humidity is present, bicarbonate will break down to carbon dioxide.

Secondly, magnesium chloride and calcium chloride mixed with bicarbonate will provide areas were the solubility product of calcium carbonate and/or magnesium carbonate will be exceeded, which would cause precipitation thereof when water is added during preparation of a concentrate or a dialysis solution.

Thirdly, even if bicarbonate is excluded to a separate cartridge, still problems would be experienced. E.g. caking and lump formation of the different components will render the dissolution thereof more difficult or even impossible when preparing the ready-for-use dialysis solution.

Fourthly, if glucose is present, a discoloration of the precursor, and later on, the ready-for-use dialysis solution would arise as a result of glucose degradation products, which should be avoided due to toxicity and limits set by authority regulations, e.g. European Pharmacopeia.

All the problems above are due to the presence of humidity within the dry precursor compositions.

In prior art this has been solved by preparing granulates of the different components and creating different layers of the different components within each granulate, like disclosed in EP0567452 or EP1714657.

However, this still may give rise to interactions between the different layers, and it is also a time-consuming matter of providing a completely and properly dissolved granulate for the preparation of the ready-for-use dialysis solution. Further, it is difficult to ensure proper composition and concentration of the different components both within the granulate and within the prepared ready-for-use dialysis solution.

SUMMARY

One object of the present invention is to provide a dialysis precursor composition which show further improved stability, limited chemical degradation and increased shelf life.

Another object of the present invention is to provide a dialysis precursor composition which give rise to further cost savings and further improved environmental benefits.

The present invention concerns a dialysis acid precursor composition for use during preparation of a dialysis acid concentrate solution and for further mixing with water, a sodium containing concentrate, and a bicarbonate containing concentrate into a ready-for-use dialysis solution. The dialysis acid precursor composition consists of powder components comprising glucose, at least one dry acid and at least one magnesium salt, and optionally potassium salt, and calcium salt. According to the invention the glucose and the at least one magnesium salt are present as anhydrous components in the dialysis acid precursor composition. Further, the dialysis acid precursor composition is sealed in a moisture-resistant container with a water vapor transmission rate less than 0.3 $g/m^2/d$ at 38° C./90% RH.

The present invention further concerns a method of providing a dialysis acid concentrate solution for dilution with water, a sodium containing concentrate, and a bicarbonate containing concentrate to produce a ready-for-use dialysis solution. According to the invention this method comprises:

(a) providing a dialysis precursor composition comprising glucose, at least one dry acid, and at least one magnesium salt, optionally potassium salt, and calcium salt, wherein the glucose and the at least one magnesium salt are present as anhydrous components in the dialysis acid precursor composition, (b) providing the dialysis precursor composition in a sealed, moisture-resistant container with a water vapor transmission rate less than 0.3 $g/m^2/d$ at 38° C./90% RH, and (c) adding a prescribed volume of water to the dialysis precursor composition in the container and mixing thereof, thereby providing the dialysis acid concentrate as a solution.

The present invention further concerns use of the dialysis acid precursor composition for preparing a dialysis acid concentrate solution.

Finally, the present invention concerns use of the dialysis acid precursor composition for preparing a dialysis solution.

Other embodiments of the present invention is evident from the description below and the dependent claims.

DETAILED DESCRIPTION

A wide variety of different combinations and partitions of dry powder components of normal dialysis solutions like potassium chloride, magnesium chloride, calcium chloride, glucose, sodium chloride, sodium bicarbonate, dry acids like citric acid, glucono-δ-lactone, etc. were prepared and put in a forced stability study. Matters like caking, lump formation, discoloration and dissolution rate were investigated after 1 month, 4 months and 10 months storage time.

It was identified that, as expected earlier, sodium bicarbonate needs to be separated from the other components due to carbon dioxide formation, calcium carbonate precipitation, and magnesium carbonate precipitation. However, when combining the remaining components of a normal dialysis solution, the crystalline water attached to glucose and magnesium chloride caused problems with caking and lump formation within the powder compositions and discoloration of glucose. By replacing glucose with anhydrous glucose and by replacing magnesium chloride hexahydrate with anhydrous magnesium chloride, or another magnesium salt not containing any crystalline water, the powder composition remained stable, free flowing and no discoloration evolved. Thus, in order to make sure that a stable composition is provided the container material used for storing the composition should be moisture-resistant and not allow passage of an amount equal to or above the amount which equals the crystalline water normally attached with the magnesium salt. This is achieved with a container material having a water vapor transmission rate less than 0.3 $g/m^2/d$ at 38° C./90% RH.

In another embodiment the container material has a water vapor transmission rate less than 0.2 $g/m^2/d$ at 38° C./90% RH.

In another embodiment the container material has a water vapor transmission rate between 0.05-0.3 $g/m^2/d$ at 38° C./90% RH.

In even another embodiment the container material has a water vapor transmission rate between 0.05-0.2 $g/m^2/d$ at 38° C./90% RH.

In another embodiment the container material has a water vapor transmission rate between 0.1-0.3 $g/m^2/d$ at 38° C./90% RH.

In even another embodiment the container material has a water vapor transmission rate between 0.1-0.2 g/m$^2$/d at 38° C./90% RH.

According to the invention the dialysis acid precursor composition consists of powder components comprising glucose, at least one dry acid and at least one magnesium salt, and optionally potassium salt, and calcium salt, wherein the glucose and the at least one magnesium salt are present as anhydrous components in the dialysis acid precursor composition within the moisture-resistant container.

In other embodiments of the present invention the at least one dry acid is selected from the group comprising of lactic acid, citric acid, gluconic acid, glucono-δ-lactone, N-acetyl cysteine and α-lipoic acid. Thus, a combination of dry acids may be used within the dialysis acid precursor composition, and by providing a combination of different dry acids, other functions and effects, apart from the acidic function, may be provided, like for instance antioxidative effects (as with gluconic acid, glucono-δ-lactone, N-acetyl cysteine and α-lipoic acid), anticoagulation effects (as with citric acid) and so forth.

In even further embodiments the at least one magnesium salt in the dialysis acid precursor composition, is selected from the group comprising of anhydrous magnesium chloride, magnesium gluconate, magnesium citrate (trimagnesium dicitrate), magnesium lactate, and magnesium α-ketoglutarate. Also here a combination of different magnesium salts may be used in order to tailor specific add-on features, like antioxidative effects from magnesium gluconate, or anticoagulation effects from magnesium citrate, and so forth.

In one embodiment the at least one magnesium salt in the dialysis acid precursor composition is selected from the group comprising of magnesium gluconate, magnesium citrate and magnesium lactate.

In other embodiments, in which calcium salt is present, the calcium salt in the dialysis acid precursor composition, is at least one chosen from the group comprising of calcium chloride dihydrate, calcium chloride monohydrate, anhydrous calcium chloride, calcium gluconate, calcium citrate, calcium lactate, and calcium α-ketoglutarate. Thus, also here a combination of different calcium salts may be used.

In another embodiment, the calcium salt is at least one chosen from the group comprising of anhydrous calcium chloride, calcium gluconate, calcium citrate and calcium lactate.

In another embodiment, the calcium salt is at least one chosen from the group comprising of calcium gluconate, calcium citrate and calcium lactate.

In one embodiment the dialysis precursor composition is provided in a specific amount and is configured to be mixed with a prescribed volume of water within the moisture-resistant container to provide a dialysis acid concentrate solution. Thus, the moisture-resistant container is configured to receive and dispense solutions up to the prescribed volume.

In one embodiment the prescribed volume may be within the range of from 0.3 to 8 L.

In another embodiment the prescribed volume may be within the range of from 5-20 L.

In even another embodiment the prescribed volume may be within the range of 300-1000 L.

Further, in one embodiment the dialysis acid concentrate solution is configured and provided to be diluted within the range of 1:30 to 1:200 with water, a sodium containing concentrate, and a bicarbonate containing concentrate.

The present invention further concerns a method of providing a dialysis acid concentrate solution. The dialysis acid concentrate solution is further intended to be mixed with additional water, a sodium containing concentrate, and a bicarbonate containing concentrate to provide a ready-for-use dialysis solution. According to the invention such a method comprises (a) providing a dialysis precursor composition comprising glucose, at least one dry acid, and at least one magnesium salt, optionally potassium salt, and calcium salt, wherein the glucose and the at least one magnesium salt are present as anhydrous components in the dialysis acid precursor composition, (b) providing the dialysis precursor composition in a sealed, moisture-resistant container with a water vapor transmission rate less than 0.3 g/m$^2$/d at 38° C./90% RH, and (c) adding a prescribed volume of water to the dialysis precursor composition in the container and mixing thereof, thereby providing the dialysis acid concentrate as a solution.

Glucose is provided in such a quantity in the moisture-resistant container that a concentration of 30-400 g/L is provided in the dialysis acid concentrate solution when a prescribed volume of water has entered into the moisture-resistant container.

The dry acid is provided in such a quantity in the moisture-resistant container that a concentration within the range of 60-800 mEq/L H$^+$ (acid) is provided in the dialysis acid concentrate solution when a prescribed volume of water has entered into the moisture-resistant container.

Further, the at least one magnesium salt is provided in such a quantity in the moisture-resistant container that a concentration within the range of 7.5-150 mM magnesium ions is provided in the dialysis acid concentrate solution when a prescribed volume of water has entered into the moisture-resistant container.

If present, the calcium salt is provided in such a quantity in the moisture-resistant container that a concentration within the range of 30-500 mM calcium ions is provided in the dialysis acid concentrate solution when a prescribed volume of water has entered into the moisture-resistant container.

If present, potassium salt is provided in such a quantity in the moisture-resistant container that a concentration within the range of 0-800 mM potassium ions is provided in the dialysis acid concentrate solution when a prescribed volume of water has entered into the moisture-resistant container.

In one embodiment the dry dialysis acid precursor composition comprises the different components in such an amount that when the dry dialysis acid precursor composition has been dissolved and mixed with water, a sodium concentrate, and a bicarbonate concentrate it provides a ready-for-use dialysis solution comprising from about 130-150 mM of sodium ions, from about 0 to 4 mM of potassium ions, from about 1-2.5 mM of calcium ions, from about 0.25 to 1 mM of magnesium ions, from about 0 to 2% (g/l) glucose from about 85 to 134 mM chloride ions, from about 2 to 4 mEq/L acid, and from about 20 to 40 mEq/L bicarbonate ions.

Thus, the present invention provides a prepackaged container with a dry dialysis acid precursor composition for use during preparation of a dialysis acid concentrate solution and for mixing with water, a sodium containing concentrate, and a bicarbonate containing concentrate into a ready-for-use dialysis solution, wherein the dialysis acid precursor composition consist of powder components comprising glucose, at least one dry acid and at least one magnesium salt. Optionally the dialysis acid precursor composition further comprises potassium salts, and calcium salts. According to the invention the glucose and the at least one magnesium salt is present as anhydrous component in the dialysis acid precursor composition and the dialysis acid precursor composition is sealed in a moisture-proof container with a water vapor transmission rate less than 0.3 g/m²/d at 38° C./90% RH.

By using anhydrous magnesium chloride powder in a dry dialysis acid precursor composition, the anhydrous component will act as desiccants if any water would be transported into the bag.

EXAMPLES

By way of example, and not limitation, the following examples identify a variety of dialysis acid precursor compositions pursuant to embodiments of the present invention.

In examples 1-5, the tables show the content of dialysis acid precursor compositions for dilution 1:35. The prescribed volume of each dialysis acid concentrate solution (DACS in tables below) is 5.714 L, and the final volume of each ready-for-use dialysis solution (RFUDS in tables below) is 200 L.

Example 1

| Ingredient | Amount (g) | Conc in DACS (mM) | Conc in RFUDS (mM) |
| --- | --- | --- | --- |
| Potassium chloride | 29.81 | 70 | 2 |
| Magnesium gluconate | 41.46 | 17.5 | 0.5 |
| Calcium chloride dihydrate | 44.10 | 52.5 | 1.5 |
| Citric acid | 38.42 | 35 | 1 |
| Glucose anhydrous | 200 | 194 | 5.55 |

Example 2

| Ingredient | Amount (g) | Conc in DACS (mM) | Conc in RFUDS (mM) |
| --- | --- | --- | --- |
| Potassium chloride | 29.81 | 70 | 2 |
| Magnesium lactate | 20.24 | 17.5 | 0.5 |
| Calcium gluconate | 129.1 | 52.5 | 1.5 |
| Citric acid | 38.42 | 35 | 1 |
| Glucose anhydrous | 200 | 194 | 5.55 |

Example 3

| Ingredient | Amount (g) | Conc in DACS (mM) | Conc in RFUDS (mM) |
| --- | --- | --- | --- |
| Potassium chloride | 29.81 | 70 | 2 |
| Trimagnesium dicitrate | 15.04 | 5.83 | 0.167 |
| Calcium gluconate | 129.1 | 52.5 | 1.5 |
| Citric acid | 38.42 | 35 | 1 |
| Glucose anhydrous | 200 | 194 | 5.55 |

Example 4

| Ingredient | Amount (g) | Conc in DACS (mM) | Conc in RFUDS (mM) |
| --- | --- | --- | --- |
| Potassium chloride | 29.81 | 70 | 2 |
| Trimagnesium dicitrate | 15.04 | 5.83 | 0.167 |
| Calcium chloride dihydrate | 44.10 | 52.5 | 1.5 |
| Glucono-delta-lactone | 35.63 | 35 | 1 |
| Citric acid | 30.73 | 28 | 0.8 |
| Glucose anhydrous | 200 | 194 | 5.55 |

Example 5

| Ingredient | Amount (g) | Conc in DACS (mM) | Conc in RFUDS (mM) |
| --- | --- | --- | --- |
| Potassium chloride | 29.81 | 70 | 2 |
| Trimagnesium dicitrate | 15.04 | 5.83 | 0.167 |
| Calcium chloride anhydrous | 33.30 | 52.5 | 1.5 |
| Glucono-delta-lactone | 142.5 | 140 | 4 |
| Glucose anhydrous | 200 | 194 | 5.55 |

In example 6-9, the tables show the content of a dry acid precursor composition for dilution 1:200. The prescribed volume of each dialysis acid concentrate solution (DACS in tables below) is 1 L, and the final volume of each ready-for-use dialysis solution (RFUDS in tables below) is 200 L.

Example 6

| Ingredient | Amount (g) | Conc in DACS (mM) | Conc in RFUDS (mM) |
| --- | --- | --- | --- |
| Potassium chloride | 59.64 | 800 | 4 |
| Magnesium gluconate | 41.46 | 100 | 0.5 |
| Calcium chloride dihydrate | 51.45 | 350 | 1.75 |
| Citric acid | 38.42 | 200 | 1 |
| Glucose anhydrous | 200 | 1111 | 5.55 |

Example 7

| Ingredient | Amount (g) | Conc in DACS (mM) | Conc in RFUDS (mM) |
| --- | --- | --- | --- |
| Trimagnesium dicitrate | 15.04 | 33.4 | 0.167 |
| Calcium gluconate | 150.6 | 350 | 1.75 |
| Citric acid | 38.42 | 200 | 1 |
| Glucose anhydrous | 200 | 1111 | 5.55 |

Example 8

| Ingredient | Amount (g) | Conc in DACS (mM) | Conc in RFUDS (mM) |
| --- | --- | --- | --- |
| Potassium chloride | 29.82 | 400 | 2 |
| Magnesium lactate | 20.24 | 100 | 0.5 |

-continued

| Ingredient | Amount (g) | Conc in DACS (mM) | Conc in RFUDS (mM) |
|---|---|---|---|
| Calcium chloride dihydrate | 44.10 | 300 | 1.5 |
| Glucono-delta-lactone | 35.63 | 200 | 1 |
| Citric acid | 30.74 | 160 | 0.8 |
| Glucose anhydrous | 200 | 1111 | 5.55 |

Example 9

| Ingredient | Amount (g) | Conc in DACS (mM) | Conc in RFUDS (mM) |
|---|---|---|---|
| Potassium chloride | 59.64 | 800 | 4 |
| Magnesium gluconate | 41.46 | 100 | 0.5 |
| Calcium chloride dihydrate | 22.22 | 200 | 1 |
| Citric acid | 38.42 | 200 | 1 |
| Glucose anhydrous | 200 | 1111 | 5.55 |

Tests

Tests has been performed to study the stability of different dry powder compositions, both according to embodiments of the present invention as well as comparisons. Parameters like caking, lumping and discoloration were evaluated.

Methods

Plastic films, was welded into bags with 1 compartment.

Composition 1

The amount of powder components of potassium chloride, anhydrous magnesium chloride, calcium chloride dihydrate, anhydrous glucose, and citric acid necessary to produce 230 L of dialysis fluid were filled into the plastic bags, with a water vapor transmission rate of 0.11 g/m²/d at 38° C./90% RH. The bags were sealed and incubated in 30° C., 65% RH, and in 40° C., 75% RH, respectively.

Composition 2

The amount of powder components of potassium chloride, anhydrous magnesium chloride, anhydrous calcium chloride, anhydrous glucose, and citric acid necessary to produce 230 L of dialysis fluid were filled into plastic bags, with a water vapor transmission rate of 0.11 g/m²/d at 38° C./90% RH. The bags were sealed and incubated in 30° C., 65% RH, and in 40° C., 75% RH, respectively.

Comparison Composition 3

The amount of powder components of potassium chloride, anhydrous magnesium chloride, calcium chloride dihydrate, anhydrous glucose, and citric acid necessary to produce 230 L of dialysis fluid were filled into plastic bags, with a water vapor transmission rate of 2.7 g/m²/d at 38° C./90% RH. The bags were sealed and incubated in 30° C., 65% RH, and in 40° C., 75% RH, respectively.

Results

Compositions 1 and 2 have proven to stay stable for at least 6 months, while comparison composition 3 failed due to formation of brown lumps after less than 1 month.

It should be understood that various changes and modifications to the embodiments described herein will be apparent to those skilled in the art. Such changes and modifications may be made without departing from the spirit and scope of the present invention and without diminishing its attendant advantages. It is therefore intended that such changes and modifications be covered by the appended claims.

The invention is claimed as follows:

1. A dialysis acid precursor composition product comprising:
    an anhydrous powdered composition including a sodium containing concentrate, a bicarbonate containing concentrate, a dry acid and a magnesium salt,
    a calcium salt in a hydrate form, and
    a sealed moisture-resistant container including a single chamber housing the anhydrous powdered composition and the calcium salt in the hydrate form, wherein the container has a water vapor transmission rate less than 0.3 g/m²/d at 38° C./90% RH, and wherein the dialysis acid precursor composition product remains stable for at least six months.

2. The dialysis acid precursor composition product of claim 1, wherein the dry acid includes at least one of lactic acid, citric acid, gluconic acid, glucono-δ-lactone, N-acetyl cysteine and α-lipoic acid.

3. The dialysis acid precursor composition product of claim 1, wherein the magnesium salt includes at least one of anhydrous magnesium chloride, magnesium gluconate, magnesium citrate, magnesium lactate, and magnesium α-ketoglutarate.

4. The dialysis acid precursor composition product of claim 1, wherein the calcium salt in the hydrate form includes at least one of calcium chloride, calcium gluconate, calcium citrate, calcium lactate, and calcium α-ketoglutarate in a hydrate form.

5. The dialysis acid precursor composition product of claim 1, wherein the water vapor transmission rate is less than 0.2 g/m²/d at 38° C./90% RH.

6. The dialysis acid precursor composition product of claim 1, wherein the water vapor transmission rate is greater than 0.1 g/m²/d at 38° C./90% RH.

7. The dialysis acid precursor composition product of claim 1, wherein the container is configured to receive water which mixes with the anhydrous powdered composition and the calcium salt in the hydrate form in the container to provide a dialysis acid concentrate solution.

8. The dialysis acid precursor composition product of claim 7, wherein the magnesium salt is in a quantity such that a concentration of 7.5-50 mM magnesium ions is provided in the dialysis acid concentrate solution.

9. The dialysis acid precursor composition product of claim 7, wherein the calcium salt in the hydrate form is provided in a quantity such that a concentration of 300-500 mM calcium ions is provided in the dialysis acid concentrate solution.

10. The dialysis acid precursor composition product of claim 7, wherein the dry acid is in a quantity such that a concentration of 60-800 mEq/L H+(acid) is provided in the dialysis acid concentrate solution.

11. The dialysis acid precursor composition product of claim 7, wherein the anhydrous powdered composition includes glucose in a quantity such that a concentration of 30-400 g/L is provided in the dialysis acid concentrate solution.

12. The dialysis acid precursor composition product of claim 1, which is configured to remain stable for at least 6 months when incubated in 30° C./65% RH or 40° C./75% RH.

* * * * *